(12) United States Patent
Yokoyama et al.

(10) Patent No.: US 8,723,996 B2
(45) Date of Patent: May 13, 2014

(54) IMAGING APPARATUS, IMAGING SYSTEM, SIGNAL PROCESSING METHOD AND PROGRAM

(75) Inventors: Keigo Yokoyama, Honjo (JP); Tadao Endo, Honjo (JP); Toshio Kameshima, Kumagaya (JP); Tomoyuki Yagi, Honjo (JP); Katsuro Takenaka, Honjo (JP)

(73) Assignee: Canon Kabushiki Kaisha, Tokyo (JP)

( * ) Notice: Subject to any disclaimer, the term of this patent is extended or adjusted under 35 U.S.C. 154(b) by 591 days.

(21) Appl. No.: 12/744,124

(22) PCT Filed: Jan. 20, 2009

(86) PCT No.: PCT/JP2009/051145
§ 371 (c)(1),
(2), (4) Date: May 21, 2010

(87) PCT Pub. No.: WO2009/093725
PCT Pub. Date: Jul. 30, 2009

(65) Prior Publication Data
US 2010/0277592 A1    Nov. 4, 2010

(30) Foreign Application Priority Data
Jan. 24, 2008  (JP) .................................. 2008-014194

(51) Int. Cl.
*H04N 3/14*    (2006.01)
*H04N 5/335*    (2011.01)

(52) U.S. Cl.
USPC ........... 348/294; 348/298; 348/302; 348/308; 348/312

(58) Field of Classification Search
USPC .................... 348/294, 298, 302, 308, 312; 250/208.1; 257/290–292; 378/91, 98.8, 378/98.11, 98.12
See application file for complete search history.

(56) References Cited

U.S. PATENT DOCUMENTS 6,952,464 B2    10/2005    Endo .......................... 378/98.11
6,985,555 B2    1/2006    Endo .......................... 378/98.11
(Continued)

FOREIGN PATENT DOCUMENTS

EP    1879051 A2    1/2008
JP    11-341361 A    12/1999
(Continued)

OTHER PUBLICATIONS

Office Action dated Jan. 31, 2012, issued in counterpart PRC Patent Application No. 200980102591.0, with translation.

*Primary Examiner* — Yogesh Aggarwal
(74) *Attorney, Agent, or Firm* — Fitzpatrick, Cella, Harper & Scinto

(57) ABSTRACT

A read out operation for reading out image data from a conversion circuit irradiated with a radiation, and a read out operation for reading out offset image data from the conversion circuit without irradiated with a radiation are selectively conducted, a control is conducted to repeat at a plurality of times the operation for reading out the offset image data, offset data corresponding to each pixel is extracted from one of the plurality of the offset image data to generate corrective offset image data such that offset data corresponding to all the pixels in a row of the matrix is not extracted from one of the plurality of offset image data, and the corrective offset image data is subtracted from the image data to perform an offset correction to render line noise less noticeable, for an offset correction without line noise by a simple signal processing to be provided.

20 Claims, 7 Drawing Sheets

(56) References Cited

U.S. PATENT DOCUMENTS

| | | | |
|---|---|---|---|
| 7,026,608 B2 * | 4/2006 | Hirai ........................ | 250/252.1 |
| 7,342,221 B2 | 3/2008 | Takenaka et al. .......... | 250/252.1 |
| 7,381,963 B2 | 6/2008 | Endo et al. ............... | 250/370.09 |
| 7,403,594 B2 | 7/2008 | Endo et al. .................. | 378/114 |
| 7,421,063 B2 | 9/2008 | Takenaka et al. ............ | 378/116 |
| 7,476,027 B2 | 1/2009 | Takenaka et al. ............ | 378/207 |
| 7,514,663 B2 | 4/2009 | Yagi et al. .................. | 250/208.1 |
| 7,532,706 B2 | 5/2009 | Kameshima et al. ........... | 378/98 |
| 7,564,038 B2 | 7/2009 | Endo et al. ............... | 250/370.11 |
| 7,573,038 B2 | 8/2009 | Yokoyama et al. ....... | 250/370.09 |
| 7,613,277 B2 | 11/2009 | Takenaka et al. ............ | 378/116 |
| 7,718,973 B2 | 5/2010 | Endo et al. ............... | 250/370.08 |
| 2003/0185342 A1 * | 10/2003 | Petrick et al. ................ | 378/98.8 |
| 2003/0190088 A1 | 10/2003 | Kobayashi ................... | 382/275 |
| 2004/0017891 A1 | 1/2004 | Endo .......................... | 378/98.8 |
| 2005/0088554 A1 | 4/2005 | Scott-Thomas et al. ...... | 348/294 |
| 2007/0210258 A1 | 9/2007 | Endo et al. ............... | 250/370.09 |
| 2007/0290143 A1 | 12/2007 | Kameshima et al. .... | 250/370.09 |
| 2008/0226031 A1 | 9/2008 | Yokoyama et al. .......... | 378/98.7 |
| 2008/0239111 A1 * | 10/2008 | Jiang ............................ | 348/243 |
| 2009/0086915 A1 | 4/2009 | Takenaka et al. ............ | 378/116 |
| 2009/0256079 A1 | 10/2009 | Endo et al. ............... | 250/370.08 |
| 2009/0272909 A1 | 11/2009 | Takenaka et al. ........ | 250/370.09 |
| 2009/0323897 A1 | 12/2009 | Kameshima et al. ......... | 378/116 |
| 2010/0148080 A1 | 6/2010 | Endo et al. ............... | 250/370.08 |

FOREIGN PATENT DOCUMENTS

| | | |
|---|---|---|
| JP | 2001-235794 | 8/2001 |
| JP | 2004-007551 | 1/2004 |
| JP | 3887420 | 2/2007 |
| JP | 2007-300183 | 11/2007 |
| WO | WO 97/28641 | 8/1997 |

* cited by examiner

OFFSET DATA
OF N-SETS

IMAGING APPARATUS, IMAGING SYSTEM, SIGNAL PROCESSING METHOD AND PROGRAM

TECHNICAL FIELD

The present invention relates to an imaging apparatus, an imaging system, a signal processing method and a program, and relates to an offset correction technique related to a photographed image.

BACKGROUND ART

A radiation imaging apparatus as an example of an imaging apparatus converts incident energy, such as a radiation or a light incident to a conversion element, such as photoelectric conversion elements, into an electric charge, and reads out, for each pixel, an electric signal based on the electric charge. Such an electric signal is hereinafter referred to as a pixel signal, and a collection of one image worth of pixel signals is referred to as an image signal. The read out image signal is used as data through various types of signal processing, such as digital processing, or printed or displayed as image data, which is a collection of one image worth of data. The image signal derived from the conversion element is subject to an offset correction especially when the signal is used as image data. The offset correction is performed by subtracting offset image data from the image data, for example. The offset image data is a collection of one image worth of offset data based on electric signals based on the electric charge caused by dark current accumulated on the conversion element when no radiation or light has irradiated the conversion element. The electric signal based on the electric charge caused by dark current accumulated on the conversion element when no radiation or light has irradiated the conversion element is referred to as a dark output pixel signal, and a collection of one image worth of dark output pixel signals is referred to as a dark output image signal.

For example, a low-noise offset correction has been proposed in U.S. Patent Application Publication No. 2004/0017891, which described that an offset correction is performed by subtracting from radiation image data, corrected image data including a plurality of offset image data that have been averaged. Hereinafter, in an image generated based on image data (imaging output) acquired from a radiation imaging apparatus, the variation in the output over the entire image is referred to as random noise. Further, the variation in the average output of each pixel group arranged in the perpendicular direction to signal wirings (along driving wirings), among the pixels arranged in a matrix, is referred to as line noise. U.S. Patent Application Publication No. 2003/0190088 described a suitable circuit structure for line noise reduction, in which image processing is performed, which detects whether or not line noise is included in the imaging output based on the acquired image signals, and, if line noise is detected, eliminates a line noise component.

DISCLOSURE OF THE INVENTION

In an imaging apparatus, which arranges a plurality of pixels in a two-dimensional matrix, each pixel including a conversion element, and performs active matrix driving to acquire an image, noise along a driving wiring (line noise) sometimes mixed unexpectedly. There is a problem that, in an image after an offset correction, when the ratio of line noise to random noise is large, image quality is reduced.

However, in the technique described in U.S. Patent Application Publication 2004/0017891, since each offset image data has independent line noise, a sufficient correction cannot be performed. In the technique described in U.S. Patent Application Publication 2003/0190088, independent line noise is detected and calculated for each imaging output (image data). Therefore, detection and calculation become more complicated. In addition, since complicated calculation processing is performed every time image data is acquired, the time-consuming detection and calculation are needed every time image data is acquired. Thus, the technique is not suitable for photographing moving images.

An object of the present invention is to provide an imaging apparatus capable of performing an offset correction to render line noise less noticeable with simple signal processing.

An imaging apparatus of the present invention comprising: a conversion unit having a plurality of pixels arranged in a matrix, each pixel including a conversion element converting a radiation or a light into an electric charge; a read out unit for reading out an electric signal group according to the plurality of conversion elements based on the electric charge of conversion elements; a control unit for conducting selectively a first read out operation and a second read out operation, wherein the first read out operation is an operation for reading out a first electric signal group from the conversion unit irradiated with the radiation by the read out unit, the second read out operation is an operation for reading out a second electric signal group from the conversion unit without irradiated with the radiation by the read out unit, and the control unit conducts a control to repeat at a plurality of times the second read out operation; and a signal processing unit for processing the electric signal group output from the read out unit, is characterized in that the signal processing unit generates a third electric signal group by deriving, from the plurality of the second electric signal groups, electric signals, each one corresponding to each one of the pixels, such that not all electric signals of the pixels in a row of the matrix are derived from one of the plurality of second electric signal groups, and the signal processing unit subtracts the third electric signal group from the first electric signal group.

An imaging system of the present invention is characterized by comprising the imaging apparatus, and a radiation generator for generating a radiation.

A signal processing method in driving an imaging apparatus of the present invention comprising: a conversion unit having a plurality of pixels arranged in a matrix, each pixel including a conversion element converting a radiation or a light into an electric charge; and a read out unit for reading out an electric signal group according to the plurality of conversion elements based on the electric charge of conversion elements, is characterized by comprising a first read out step of reading out, by the read out unit, electric signals based on the electric charge converted by the plurality of conversion elements, from the conversion unit irradiated with the radiation, and outputting the electric signal group as a first electric signal group; a second read out step of reading out, by the read out unit, electric signals based on the electric charge converted by the plurality of conversion elements, from the conversion unit without irradiated with the radiation, and outputting the electric signal group as a second electric signal group; and a signal processing step of repeating at a plurality of times the second read out step, generating a third electric signal group by deriving, from the plurality of the second electric signal groups, electric signals, each one corresponding to each one of the pixels, such that not all electric signals of the pixels in a row of the matrix are derived from one of the plurality of second electric signal groups, and subtracting the third electric signal group from the first electric signal group.

A program of the present invention that causes a computer to execute a signal processing method in driving an imaging apparatus comprising: a conversion unit having a plurality of pixels arranged in a matrix, each pixel including a conversion element converting a radiation or a light into an electric charge; and a read out unit for reading out an electric signal group according to the plurality of conversion elements based on the electric charge of conversion elements, is characterized by causing the computer to execute; a first read out step of reading out, by the read out unit, electric signals based on the electric charge converted by the plurality of conversion elements, from the conversion unit irradiated with the radiation, and deriving the electric signal group as a first electric signal group; a second read out step of reading out, by the read out unit, electric signals based on the electric charge converted by the plurality of conversion elements, from the conversion unit without irradiated with the radiation, and deriving the electric signal group as a second electric signal group; and a signal processing step of repeating at a plurality of times the second read out step, generating a third electric signal group by deriving, from the plurality of the second electric signal groups, electric signals, each one corresponding to each one of the pixels, such that not all electric signals of the pixels in a row of the matrix are derived from one of the plurality of second electric signal groups, and subtracting the third electric signal group from the first electric signal group.

According to the present invention, the second read out operation is controlled to be repeated at a plurality of times to generate a third electric signal group by deriving, from one of the plurality of second electric signal groups, electric signals, each one corresponding to each one of the pixels, and to subtract the third electric signal group from the first electric signal group. The third electric signal group is generated such that not all electric signals of the pixels in a row of the matrix are derived from one of the plurality of the second electric signal groups. Accordingly, the third electric signal group including electric signals of the plurality of the second groups in each row of the matrix can be used to perform an offset correction, thus an excellent image in which line noise is less noticeable can be acquired with simple signal processing.

Further features of the present invention will become apparent from the following description of exemplary embodiments with reference to the attached drawings.

BRIEF DESCRIPTION OF THE DRAWINGS

FIGS. 5A, 5B and 5C are diagrams illustrating the timing of the read out operation of the imaging apparatus according to the first exemplary embodiment.

BEST MODES FOR CARRYING OUT THE INVENTION

Exemplary embodiments of the present invention will be described below with reference to the drawings.

First Exemplary Embodiment

Figure 1:
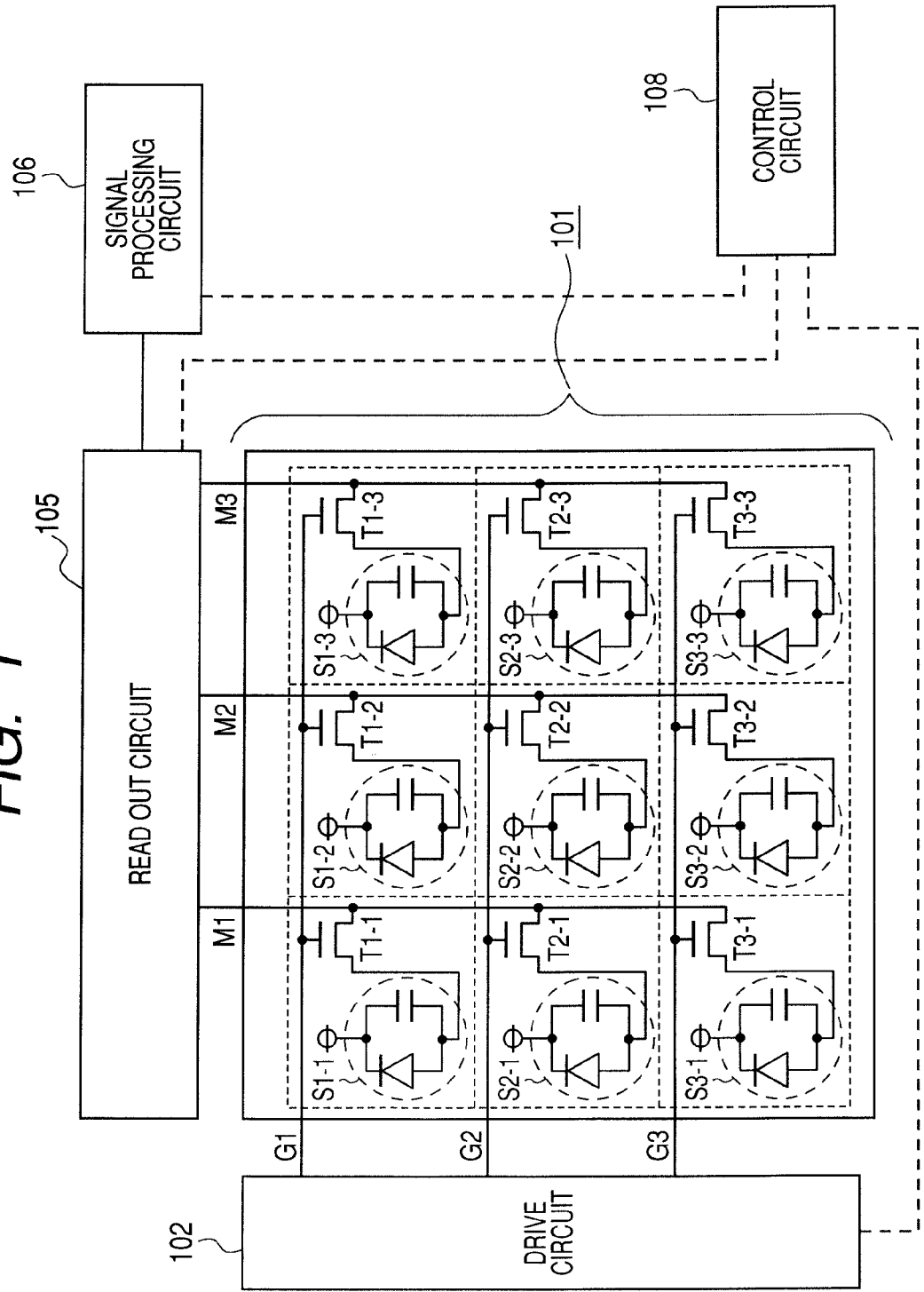
FIG. 1 is a diagram illustrating an example of a structure of an imaging apparatus according to a first exemplary embodiment.

FIG. 1 is a simplified diagram of a structure of an imaging apparatus according to a first exemplary embodiment of the present invention.

FIG. 1 illustrates, as an example, an imaging apparatus using, as a conversion element, a photoelectric conversion element made of amorphous silicon for converting a visible light into an electric charge. Note that, if the imaging apparatus is used as an imaging apparatus for capturing a radiation such as an X-ray, a phosphor, which is a wavelength converter converting the X-ray into a light of a wavelength band that the photoelectric conversion element can detect, and the photoelectric conversion element can be combined so as to be used as a conversion element. Although the present exemplary embodiment illustrates X-ray imaging, the present invention is not limited thereto; for example, a conversion element that can directly convert an X-ray into an electric charge (direct conversion element) may be provided without a phosphor. Further, a radiation in the present invention is not limited only to an X-ray. An α-ray, a β-ray, a γ-ray may be included in the category of a radiation. Note that, for purposes of illustration, in the present invention, the conversion of a radiation and a light into an electric charge is referred to as a photoelectric conversion.

In FIG. 1, Sm-n (m=1 to 3, n=1 to 3) is a photoelectric conversion element used as a conversion element for converting a radiation or a light into an electric charge, and Tm-n (m=1 to 3, n=1 to 3) is a switch element for outputting an electric signal based on an electric charge generated by the photoelectric conversion element, such as a thin film transistor (TFT). A plurality of pixels is arranged in a matrix, each of which has a conversion element such as a photoelectric conversion element, and a switch element. The driving wiring Gm transmits to the switch element a driving signal to control a conductive state and a non-conductive state of the switch element, and is electrically connected to a control terminal of the switch element. The driving wiring Gm is connected common to the switch elements of a plurality of pixels in the row direction of the matrix row by row, and a plurality of driving wirings are provided in the column direction. The signal wiring Mn transmits an output electric signal to a read out circuit, which is described later, and is electrically connected to one of a source and a drain (main terminal) of the switch element, and the read out circuit. The signal wiring Mn is connected to the switch elements of a plurality of pixels in the column direction of the matrix column by column, and a plurality of signal wirings are provided in the row direction. Note that m and n are subscripts, wherein m is a natural number of 1 to 3, and n is a natural number of 1 to 3 (hereinafter, the same). Note that for convenience, FIG. 1 illustrates a case where only three rows and three columns of pixels are arranged, but the number of pixels is arbitrary, and more pixels may be arranged as needed.

Each photoelectric conversion element Sm-n represents a photodiode and a capacity for storing electric charges generated at the photodiode with a parallel connection, and a reverse bias is applied in order to bring the photoelectric conversion element into a photoelectrically convertible state. That is to say, a cathode electrode of the photodiode is biased to + (plus). A bias wiring, which transmits to the conversion element a bias to bring the conversion element such as a photoelectric conversion element into a photoelectrically convertible state, is connected to one of the terminal of the conversion element. Although the bias wiring is generally connected common to a plurality of pixels arranged in a matrix, the bias wiring is not shown as the common wiring in FIG. 1. The electric charge photoelectrically converted by the photoelectric conversion element is stored in the capacity.

The photoelectric conversion element Sm-n at the $m^{th}$ row and $n^{th}$ column has one of the terminals connected to the bias wiring, and the other terminal is connected to the other of the source and drain (main terminal) of the switch element Tm-n at the $m^{th}$ row and $n^{th}$ column. The switch elements Tm-1 to Tm-3 in the $m^{th}$ row have the control terminals (e.g. transistor gates) thereof connected to the drive wiring Gm in the $m^{th}$ row. The photoelectric conversion elements S1-1 to S3-3 as conversion elements, the switch elements T1-1 to T3-3, the driving wirings G1 to G3, the signal wirings M1 to M3 and the bias wirings are collectively referred to as a conversion circuit 101. Note that the conversion circuit 101 in the present exemplary embodiment functions as a conversion unit in the present invention.

The drive circuit 102 is electrically connected to the driving wiring Gm, and drives the conversion circuit 101. The drive circuit 102 applies to the driving wiring Gm a driving signal having pulse-shape conduction voltage to bring the switch elements Tm-1 to Tm-3 into a conductive state, and controls the driving of the conversion circuit 101. A shift register is suitable for the drive circuit 102. Note that the drive circuit 102 in the present exemplary embodiment functions as a driving unit in the present invention.

A read out circuit 105 is electrically connected to the signal wiring Mn, and reads out an electric signal (pixel signal) output by the switch elements Tm-1 to Tm-3, and outputs one image worth of electric signals (image signals) based on the electric charge converted by the photoelectric conversion element Sm-n in the conversion circuit 101. The read out circuit 105 amplifies the parallel electric signals (pixel signals) output row by row by the photoelectric conversion elements Sm-1 to Sm-3 in the conversion circuit 101, serializes the parallel signals, and outputs one image worth of the electric signals (image signals). The output electric signal is analog-digital converted, and output as a digital image signal, which is a collection of one image worth of digital signals. Note that the read out circuit 105 in the present exemplary embodiment functions as a read out unit in the present invention. In addition, the structure of the read out circuit 105 will be described in details below with reference to FIG. 2.

A signal processing circuit 106 processes digital image signals output by the read out circuit 105, and generates and outputs image data. Note that the signal processing circuit 106 in the present exemplary embodiment functions as a signal processing unit in the present invention. A control circuit 108 serving as a control unit controls the drive circuit 102, the read out circuit 105 and the signal processing circuit 106. For example, the control circuit 108 conducts to control selectively an operation for driving the conversion circuit 101 irradiated with a radiation and reading out an image signal associated with a radiation image, and an operation for driving the conversion circuit 101 without irradiated with a radiation and reading out the image signal associated with offset. The image signal associated with the radiation image (radiation image signal) corresponds to the first image signal of the present invention, and the electric signal associated with the offset (dark output image signal) corresponds to the second image signal of the present invention.

Figure 2:
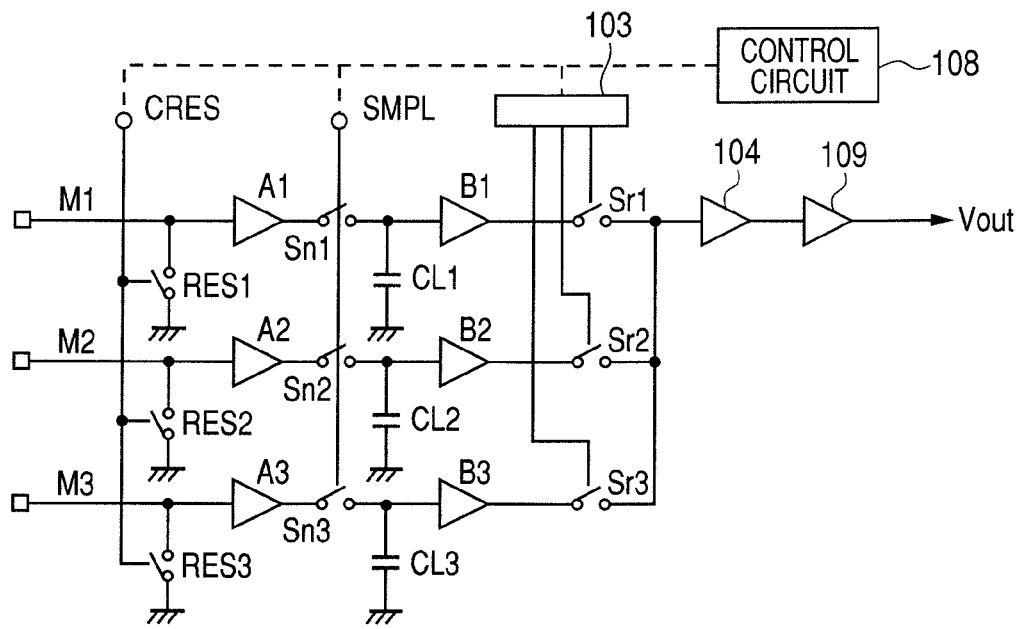
FIG. 2 is a diagram illustrating an example of a structure of a read out circuit according to the first exemplary embodiment.

Next, the structure of the read out circuit 105 will be described in details with reference to FIG. 2. FIG. 2 is a circuit diagram illustrating an example of a structure of the read out circuit 105 shown in FIG. 1. Reset switches RES1 to RES3 reset the signal wirings M1 to M3, and amplifiers A1 to A3 amplify signals conveyed through the signal wirings M1 to M3. Sampling and holing capacities CL1 to CL3 temporarily store the signals amplified by the amplifiers A1 to A3, and sampling and holing switches Sn1 to Sn3 perform sampling and holing operation. A sample/hold circuit includes a pair of sampling and holing capacities CL1 to CL3 and sampling and holing switches Sn1 to Sn3. B1 to B3 are buffer amplifiers. At least one each of the amplifiers A1 to A3, the sample/hold circuit and the buffer amplifiers B1 to B3 is provided at each of the signal wirings M1 to M3. Multiplexer switches Sr1 to Sr3 output the parallely output electric signals (pixel signals) as serialized electric signals (image signals). A shift register 103 provides a pulse in order to cause the switches Sr1 to Sr3 to execute serialization. A buffer amplifier 104 outputs the serialized signal as a signal Vout. An analog-digital converter (ADC) 109 converts analog image signals into digital image signals. Note that although according to the present exemplary embodiment, ADCs 109 is placed at a subsequent stage to the multiplexer switches Sr1 to Sr3, the read out unit in the present invention is not limited thereto. The ADC 109 may be provided at each of the signal wirings M1 to M3 at a prior stage to the multiplexer switches Sr1 to Sr3. The read out unit of the present invention suffices to be one having a function capable of outputting as digital image signals, electric signals output in parallel row by row by the conversion unit.

The reset switches RES1 to RES3, the sampling and holing switches Sn1 to Sn3, and the multiplexer switches Sr1 to Sr3 (more specifically, shift register 103) are controlled by the control circuit 108. The conductive state/non-conductive state of the switches RES1 to RES3 is controlled based on a control signal CRES from the control circuit 108, and the conductive state/non-conductive state of the switches Sn1 to Sn3 is controlled based on a control signal SMPL from the control circuit 108. The conductive state/non-conductive state of the switches Sr1 to Sr3 is controlled based on the pulse output by the shift register 103 based on the control signal from the control circuit 108.

Figure 3:
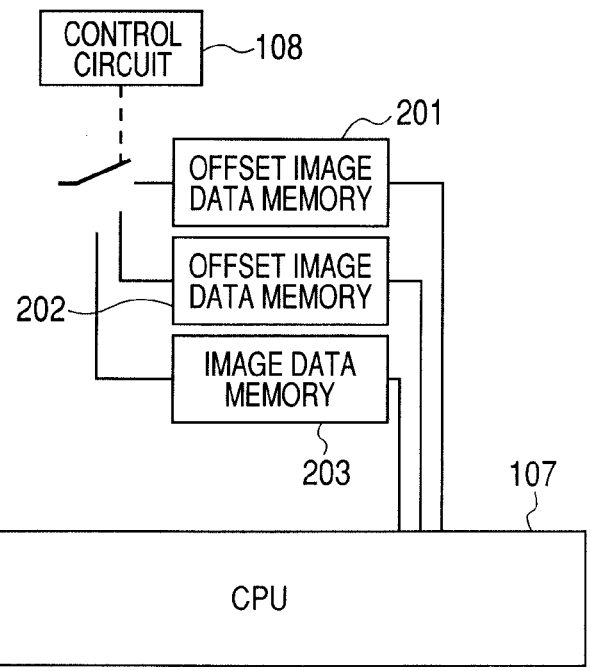
FIG. 3 is a diagram illustrating an example of a structure of a signal processing circuit according to the first exemplary embodiment.

Next, the structure of the signal processing circuit 106 will be described in details with reference to FIG. 3. FIG. 3 is a diagram illustrating an example of a structure of the signal processing circuit 106 shown in FIG. 1. The signal processing circuit 106 has a first offset image data memory 201, a second offset image data memory 202, an image data memory 203 and a CPU (central processing unit) 107.

The first and second offset image data memories 201 and 202 are storage units for storing offset image data based on dark output pixel signals acquired by performing the read out operation (second read out operation) without irradiating an X-ray on the conversion unit. The read out operation performed in order to read out the electric signals based on an X-ray or a light irradiated on the conversion unit, which is performed in order to acquire image data, is referred to as a first read out operation. Meanwhile, the read out operation, which is performed to read out from the conversion unit, electric signals generated by the conversion unit without irradiating an X-ray or light on the conversion element, in order to acquire offset image data, is referred to as a second read out operation. Each of the offset image data memories 201 and 202 stores offset image data based on one image worth of dark output image signals, therefore two images worth of offset image data are stored in the signal processing circuit 106.

The image data memory 203 is a storage unit for storing image data based on pixel signals derived by a first read out operation after an X-ray is irradiated. The CPU 107 centrally controls each function unit in the signal processing circuit 106. The CPU 107 also performs signal processing described later based on data stored in the first and second offset image data memories 201 and 202, and the image data memory 203.

Figure 4:
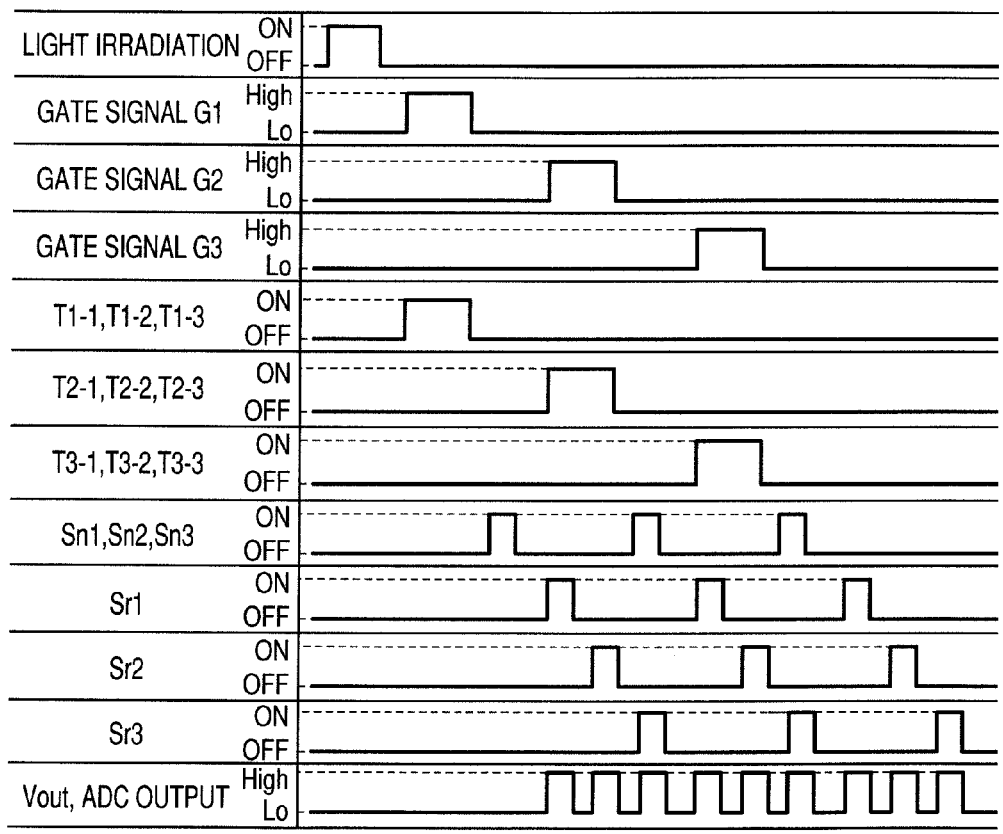
FIG. 4 is a timing chart illustrating an operation for reading out an image by the imaging apparatus according to the first exemplary embodiment.

An operation for reading out one frame (image) worth of image signals by the imaging apparatus according to the present exemplary embodiment will be described with reference to FIG. 4. FIG. 4 is a timing chart of the imaging apparatus according to the present exemplary embodiment. FIG. 4 illustrates signals input into/output from each of the function units of the conversion circuit 101, the drive circuit 102 and the read out circuit 105.

In the photoelectric conversion element Sm-n, photoelectrically converted electric charges are accumulated in the capacity that each photoelectric conversion element Sm-n has. Note that although the amount of the capacity that each photoelectric conversion element Sm-n has is assumed to be the same here, actually it may vary slightly for each photoelectric conversion element.

The order of reading out the electric signals based on the accumulated electric charges from the photoelectric conversion element Sm-n is controlled by the drive circuit 102 through the driving wiring Gm connected common to the switch element Tm-n of each pixel in a row of the matrix. More specifically, the switch elements T1-1 to T1-3 corresponding to the photoelectric conversion elements S1-1 to S1-3 in the first row are driven row by row by the driving signal provided by the drive circuit 102 through the driving wiring G1. Next, the switch elements T2-1 to T2-3 corresponding to the photoelectric conversion elements S2-1 to S2-3 in the second row are driven row by row by the driving signal provided by the drive circuit 102 through the driving wiring G2. Then, the switch elements T3-1 to T3-3 corresponding to the photoelectric conversion elements S3-1 to S3-3 in the third row are driven row by row by the driving signal provided by the drive circuit 102 through the driving wiring G3. Note that the order described herein is in arbitrary, and the order may be changed as needed. In this manner, through the switch elements driven row by row, electric signals based on the electric charges generated by the conversion element such as the photoelectric conversion element are output row by row. The drive circuit 102 is controlled by the control circuit 108.

The control circuit 108 controls the drive circuit 102 so as to provide a driving signal (gate signal) from the drive circuit 102 to the driving wirings G1 to G3. This causes the switch elements T1-1 to T1-3 in the first row to enter an on-state, and the electric signals based on the electric charges accumulated in each capacity of the photoelectric conversion elements S1-1 to S1-3 in the first row to be output in parallel row by row to each of the signal wirings M1 to M3.

The electric signals output to the signal wirings M1 to M3 are sent to the read out circuit 105 in parallel, and amplified by each of the amplifiers A1 to A3 in the read out circuit 105. At that time, the reset switches RES1 to RES3 connected to each of signal wirings M1 to M3 are in a non-conductive state.

Subsequently, when the control circuit 108 controls each of the sampling and holing switches Sn-1 to Sn-3 to be entered into a conductive state, the electric signals amplified by each of the amplifiers A1 to A3 are accumulated in each of the sampling and holing capacities CL1 to CL3, and sampled and held. The electric signals sampled and held by each of the capacities CL1 to CL3 are parallel-serial converted (multiplexed) by sequentially bringing the multiplexer switches Sr1 to Sr3 into a conductive state with the shift register 103 controlled by the control circuit 108. In this manner, the electric signals based on the electric charges converted by the photoelectric conversion element Sm-n are read out sequentially to the ADC 109 through each of the buffer amplifiers B1 to B3 and the buffer amplifier 104, and output as image signals. The output image signals are analog-digital (A/D) converted by the ADC 109, and output to the signal processing circuit 106 as image data.

By the control of the control circuit 108, the output image data is sent to and stored in the offset image data memories 201 and 202, and the image data memory 203 depending on the type of the image data. The CPU 107 uses various types of image data stored in the offset image data memories 201 and 202, and the image data memory 203 to perform signal processing, which will be described later.

Sequentially performing the operation described above row by row on the photoelectric conversion elements S2-1 to S2-3 in the second row and the photoelectric conversion elements S3-1 to S3-3 in the third row allows one image worth of imaging output (image data) to be acquired. Note that the readout of the electric signals from the next row of pixels needed not be after the electric signals read out from the previous row of pixels have been digitally converted and stored into the memory. For example, the electric signals of the next row of pixels may be read out if it is after the electric signals read out from the first row of pixels have been sampled and held in the sampling and holing capacities CL1 to CL3. That is to say, the electric signals of the second row of pixels can be read out within the time frame for performing multiplexing of the electric signals of the first row of pixels and A/D conversion.

Note that the circuit structure and operation in regards to read-out of electric signals based on the electric charges of the photoelectric conversion element Sm-n described above are one example, and other structures and methods are possible as long as the electric signal from each pixel can be read out.

In the imaging apparatus according to the present exemplary embodiment, although the drive circuit 102, the read out circuit 105, the signal processing circuit 106 and the control circuit 108 are at least connected electrically, compartmentalization of each of these circuits may sometimes be difficult. However, in the present exemplary embodiment, there is no need for each function to be separated physically, and it will suffice that each of the functions of the drive circuit 102, the read out circuit 105, the signal processing circuit 106 and the control circuit 108 are assumed by the system in its entirety. For example, one IC may assume the roles of the ADC 109, the buffer amplifier 104 and the control circuit 108.

FIGS. 5A, 5B and 5C are diagrams illustrating the timing of the read out operation of the imaging apparatus according to the present exemplary embodiment. In FIGS. 5A to 5C, the direction oriented rightward indicates the passage of time. In FIGS. 5A to 5C, an irradiation period during which the conversion unit is irradiated with an X-ray or a light is indicated by "X", and during the irradiation period "X", the imaging apparatus performs a first accumulation operation for accumulating electric signals generated by the conversion unit irradiated with the X-ray or the light. A read out period during which image data is read out from the imaging apparatus is indicated by "H", and during the read out period "H", the imaging apparatus reads out electric signals accumulated in the conversion unit. The read out operation performed during the read out period "H" corresponds to the first read out operation in the present invention. In the example shown in FIGS. 5A to 5C, "X" and "H" are represented at the ten$^{th}$ frame. Note that this is only one example, and the present invention is not limited thereto. Through the first accumulation operation and the first read out operation, the operation for acquiring image data based on the irradiated radiation or light is performed.

In FIGS. 5A to 5C, the period having the same time scale and operation of the conversion element as the irradiation period "X" but during which the conversion unit is not irradiated with an X-ray or a light is indicated by "W". "W" is a period during which the dark output pixel signals based on the electric charges caused by dark current of the conversion element such as a photoelectric conversion element are accumulated in pixels, and is referred to as a weight period. During the weight period "W", the imaging apparatus performs a second accumulation operation for accumulating the dark output pixel signals. Although a read out period for reading out offset image data from the imaging apparatus after the weight period is indicated by "F", the operation of the imaging apparatus is the same as that of the read out period "H". The difference between the period "F" and the period "H" is whether or not to be used as information to acquire radiation image data. The period "F" is referred to as an offset read out period, and the read out operation during the period is referred to as an offset read out operation. The offset read out operation corresponds to the second read out operation in the present invention. Through the second accumulation operation and the second read out operation, the operation for acquiring offset image data is performed.

FIG. 5A illustrates a case where the operation for acquiring offset image data is performed more than once. First, the imaging apparatus alternately performs the second accumulation operation at the weight period "W" and the second read out operation at the offset read out period "F". At that time, in an actual radiographic site, an X-ray technician (radiographer) positions a portion to be radiographed of a patient (subject) on an X-ray receiving surface on the imaging apparatus. Regarding the offset image data acquired in the offset read-out operation "F", since it is not known when an X-ray will be irradiated after this, only the latest two images worth of offset image data are subsequently stored in the offset image data memories 201 and 202.

After the positioning of the patient is finished, and the preparation for radiographing is complete, the X-ray technician (radiographer) issues an irradiation command through the control circuit 108. The imaging apparatus receiving the irradiation command from the control circuit 108 transitions to the first accumulation operation at the irradiation period "X". The electric signals accumulated by the first accumulation operation acquire image data by the first read out operation at the first read out period "H". At that time, the image data is stored in the image data memory 203.

In the example shown in FIG. 5A, two images worth of the offset image data stored in the offset image data memories 201 and 202 before the first read out period "H" during which read out operation of the image data is performed, are used for signal processing, which will be described later.

As shown in FIG. 5B, signal processing described later may be performed by using offset image data acquired by the second accumulation operation at the weight period "W" and the second read out operation at the offset read out period "F" after the first read out period "H". Accordingly, although corrected image data cannot be acquired immediately after the operation for acquiring the image data, storage into the offset image data memories 201 and 202 before the operation for acquiring the image data is eliminated.

As shown in FIG. 5C, the signal processing described later may be performed by using offset image data acquired by performing the operation for acquiring the offset image data once before and once after the operation for acquiring the image data. In the example shown in FIG. 5C, before the operation for acquiring the image data, the data in the first offset image data memory 201 is updated every time offset image data is acquired. The offset image data acquired after the operation for acquiring image data is stored in the second offset image data memory 202.

The data bus of the CPU 107 is connected to the data wirings of three memories 201, 202 and 203 so that three memories 201, 202 and 203 can be selected as appropriate.

In an image after an offset correction, line noise reduction is important in terms of the improvement in the image quality. In addition, there may be a feeling that something is wrong at the evaluation of the image quality when the ratio of the line noise to the random noise is large, therefore, the reduction of the ratio of the line noise to the random noise is also important in terms of the improvement in the image quality. It is more desirable that these are performed with a simple correction.

The offset correction method in the imaging apparatus according to the present exemplary embodiment will be described below. Note that while the pixel row and column numbers in the conversion circuit 101 were three rows and three columns for convenience in the imaging apparatus described above, in the following, description will be given with the pixel row and column numbers of eight rows and eight columns.

FIGS. 6A, 6B, 6C and 6D are diagrams illustrating an example of a generation method of corrective offset image data according to the present exemplary embodiment. FIGS. 6A to 6D are conceptual diagrams illustrating an example in which corrective offset image data for use in an offset correction, that is to say, for use in the subtraction from the image data, is generated from two images worth of offset image data. Here, the description is provided assuming that the corrective offset image data to be generated corresponds to a third electric signal group in the present invention. In the present exemplary embodiment, for each of the pixels (conversion elements), offset data based on one dark output pixel signal is extracted from two images worth of the offset image data, which is used for re-synthesis to generate corrective offset image data.

Figure 6A:
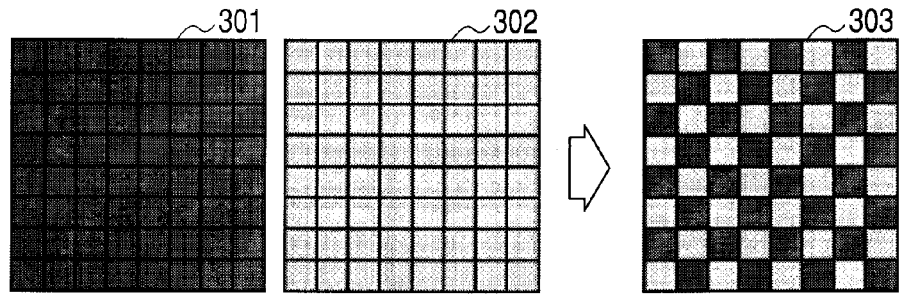
FIGS. 6A, 6B, 6C and 6D are diagrams illustrating an example of a generation method of corrective offset image data according to the first exemplary embodiment.

In an example shown in FIG. 6A, from the first offset image data 301 and the second offset image data 302 of eight rows and eight columns of pixels, corrective offset image data 303 of the eight rows and eight columns of pixels is generated. The first offset image data 301 and the second offset image data 302 are offset image data stored in the first offset image data memory 201 and the second offset image data memory 202, respectively.

In FIG. 6A, one grid of the offset image data 301 and 302 is offset data based on the dark output pixel signals of the pixels (conversion elements) arranged in a two-dimensional array. Each offset data for each pixel is captured into the CPU 107 through the data bus from the offset image data memories 201 and 202. The CPU 107 extracts the output of each pixel of the captured two images worth of offset image data 301 and 302 alternately to generate new corrective offset image data 303.

In FIG. 6A, the corrective offset image data 303 is generated by extracting and re-synthesizing the offset data of each pixel of the offset image data 301 and 302 so as to be alternately arranged in the perpendicular direction and the horizontal direction. A perpendicular direction with respect to the row direction in which the driving wiring for the conversion unit is provided is referred to as a longitudinal direction, and a horizontal direction with respect to the row direction is referred to as a lateral direction. That is to say, the corrective offset image data 303 is generated by being re-synthesized in such a way that the offset data of the pixel next to a pixel extracted from the offset image data 302 is used next to the offset data of a pixel extracted from the offset image data 301.

Figure 6B:
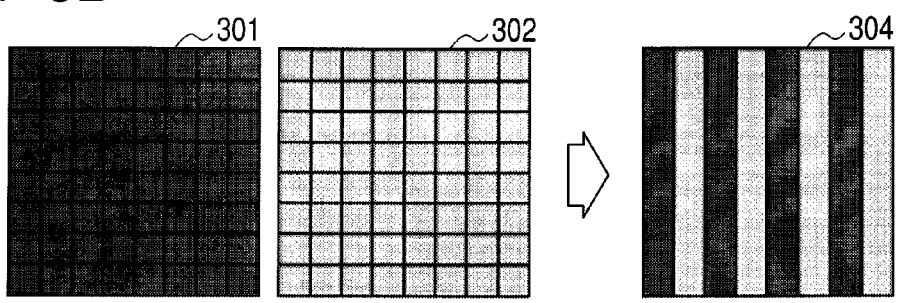

Note that, similarly to the corrective offset image data 304 shown in FIG. 6B, the offset data of each pixel of the offset image data 301 and 302 may be arranged alternately only in the lateral direction.

Figure 6C:
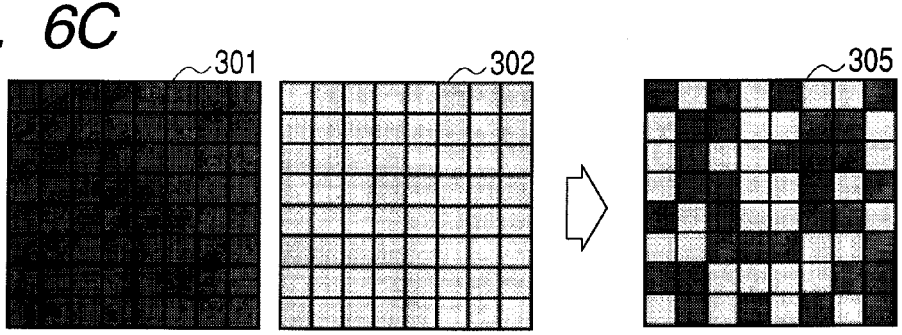
Figure 6D:
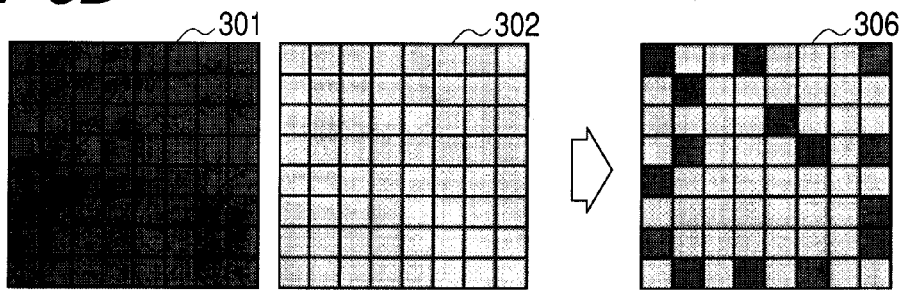

Similarly to the corrective offset image data 305 shown in FIG. 6C, the offset data of each pixel of the offset image data 301 and 302 may be randomly extracted and re-synthesized to generate corrective offset image data. However, in this case, the same number or almost the same number of the image data arranged in the lateral direction can be extracted from each of the offset image data 301 and 302. The offset data of each pixel of the corrective offset image data may include the same number or almost the same number of the offset data from the offset image data 301 and 302. Alternatively, similarly to the corrective offset image data 306 shown in FIG. 6D, the number of the offset data from the offset image data 301 and the number of the offset data from the offset image data 302 constituting the corrective offset image data 306 may be different.

In the present exemplary embodiment, when the corrective offset image data is generated from two images worth of offset image data 301 and 302, offset data from the offset image data 301 and the offset data from the offset image data 302 are used in the row direction. In other words, the corrective offset image data is generated in such a way that not all of one row of offset data is extracted in the offset image data 301 or 302. In the corrective offset image data, desirably, the offset data from the same offset image data 301 and 302 are not adjacent to each other in the lateral direction.

Performing a correction so that the mean value of each offset image data from the offset image data 301 and 302 is the same, allows the noise increase generated by a difference in the mean value to be held down when generating a corrective offset image data.

Figure 7:
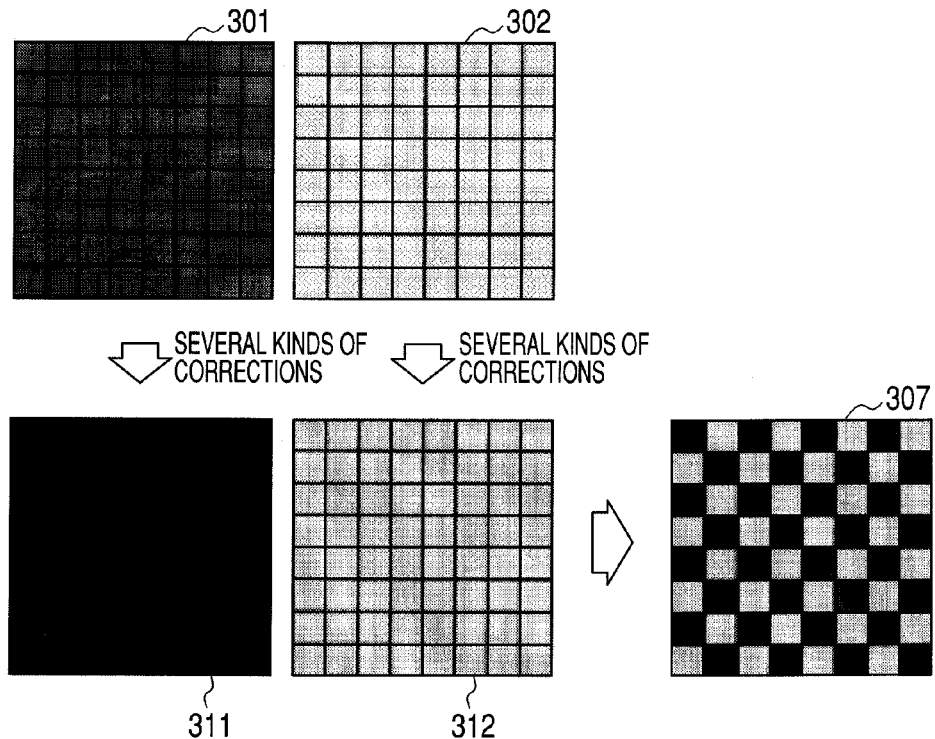
FIG. 7 is a diagram illustrating another example of the generation method of corrective offset image data according to the first exemplary embodiment.

As shown in FIG. 7, offset image data 311 and 312 acquired by applying a correction such as pixel addition and filtering to the offset image data 301 and 302 may be used to generate the corrective offset image data 307 with the above described method.

The CPU 107 uses the generated corrective offset image data and the image data stored in the image data memory 203 to further perform subtraction for each pixel. In this manner, data acquired by subtracting the corrective offset image data from the image data becomes the corrected image data after an offset correction.

As described above, the image data is offset-corrected while becoming excellent corrected image data in which the ratio of the line noise to the random noise and the line noise have been held down.

For example, in each offset image data 301 and 302, assuming that the random noise is equal to σ random, and the line noise is equal to σ Line, the ratio of the line noise to the random noise is (σ Line/σ random). In contrast to this, in the present exemplary embodiment, the line noise of the corrective offset image data shown in FIG. 6A becomes almost (σLine/√2). Therefore, the ratio of the line noise to the random noise of the offset for a correction becomes (1/√2)×(σ Line/σ random). Using the corrective offset image data to correct the image data by subtraction allows a higher quality corrected image to be obtained, compared to when only one of the offset image data 301 and 302 is used directly in the subtraction to be subtracted from the image data.

For example, it is assumed that the values of the random noise and line noise of the image data are the same as those of the offset image data. When only one of the offset image data 301 and 302 is used for direct subtraction, and subtracted from the image data, which is an example of conventional correction methods, the noise of the corrected offset image data after an offset correction becomes as follows. In the corrected image data after an offset correction with the conventional correction method, the line noise is (σ2) σ Line, and the ratio of the line noise to the random noise is (σ Line/σ random). In contrast to this, in the corrected image data after an offset correction according to the present exemplary embodiment, the line noise is ((√3)/(√2))σ Line, and the ratio of the line noise to the random noise is ((3)/2)×(σ Line/σ random).

Compared with a conventional approach in which offset image data is used for direct subtraction, the line noise and the ratio of the line noise to the random noise according to the present exemplary embodiment are reduced to ((√3)/2) =0.866.

Figure 8A:
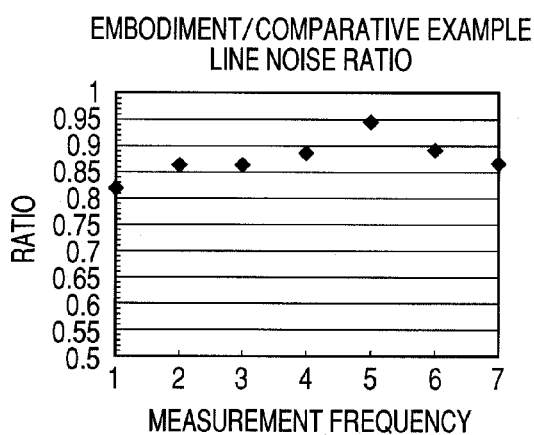
FIGS. 8A and 8B are diagrams illustrating the result of comparison between a conventional approach and a case where the present exemplary embodiment is applied.

FIG. 8A illustrates the line noise ratio when the conventional approach described above (comparative example) and the present exemplary embodiment are actually applied. Similarly, FIG. 8B illustrates the ratio of the line noise to the random noise when the conventional approach described above (comparative example) and the present exemplary embodiment are applied.

Figure 8B:
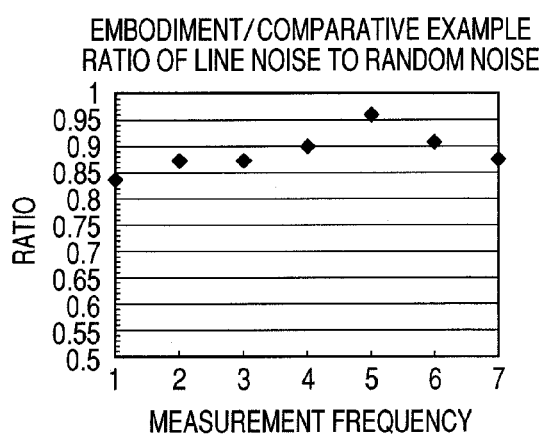

As is clear from FIGS. 8A and 8B, in the present exemplary embodiment, the line noise and the ratio of the line noise to the random noise have been improved compared to those in the conventional approach. As shown in FIG. 8A, according to the present exemplary embodiment, it is apparent that an excellent image in which the line noise is actually reduced is provided. As shown in FIG. 8B, according to the present exemplary embodiment, it is apparent that the ratio of the line noise to the random noise has been reduced, allowing an image in which the influence of the line noise is less noticeable to be provided. In particular, in cases where (σ Line/σ random)>0.1 in which lines caused by the line noise become visible in the image quality, obtaining the effect of improved line noise and ratio of the line noise to the random noise in the final image quality evaluation is facilitated.

According to the first exemplary embodiment, with simple processing and without performing complicated processing, offset components generated in the imaging apparatus during photographing can be corrected, and an excellent image in which the line noise and the ratio of the line noise to the random noise have been held down can be acquired.

Second Exemplary Embodiment

Next, a second exemplary embodiment of the present invention will be described.

According to the second exemplary embodiment, three or more images worth of offset image data for generating corrective offset image data are acquired to reduce the line noise. That is to say, three or more images worth of offset image data are used to generate corrective offset image data.

It is to be note that the description will be omitted since it is the same as the first exemplary embodiment except for the method of the corrective offset image data generation, and only how to generate the corrective offset image data according to the second exemplary embodiment will be described below. Note that the number of offset image data memory that the signal processing circuit 160 has is as much as or more than the number of offset image data used to generate the corrective offset image data.

Figure 9:
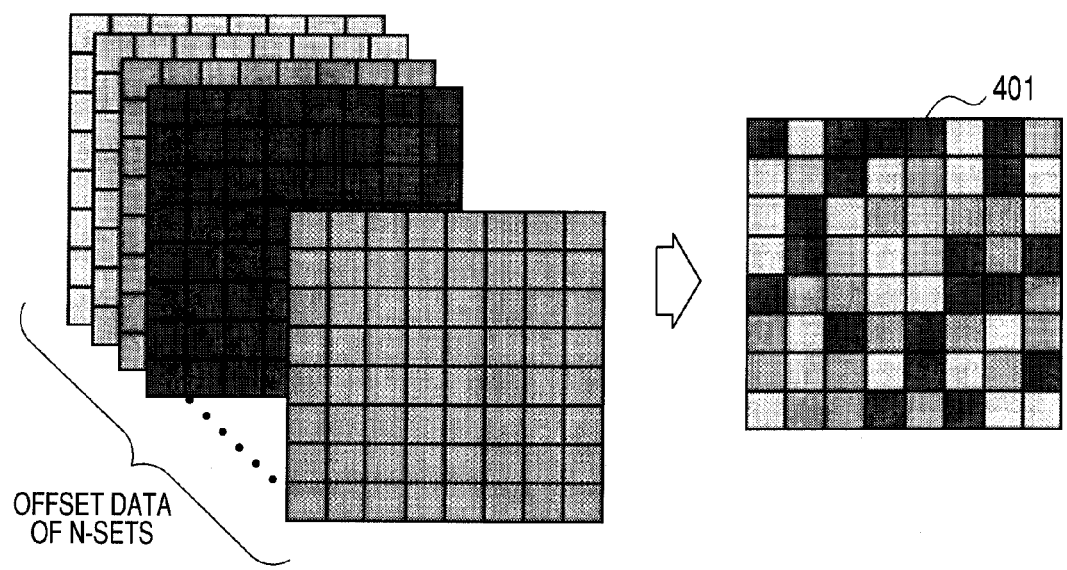
FIG. 9 is a diagram illustrating a generation method of corrective offset image data according to a second exemplary embodiment.

FIG. 9 is a diagram illustrating a generation method of corrective offset image data according to the second exemplary embodiment. In the second exemplary embodiment, the signal processing circuit 160 extracts the offset data for each pixel of the corrective offset image data 401 randomizing the offset data of the corresponding pixel respectively from N images worth of offset image data and generates the corrective offset image data 401. Note that as with the first exemplary embodiment, the timing for acquiring each offset image data may be either of before and after the image data is acquired. If the line noise is bothersome when looking at the final corrected image, the X-ray technician (radiographer) can use the control circuit 106 to instruct to freely increase the number of offset image data used for generating the corrective offset image data 401. At that time, the upper limit of the number of offset image data is equal to the amount of the offset image data memory that the signal processing circuit 106 has.

It is assumed that from each of the N images worth of offset image data, the same number of offset data has been extracted for each pixel to generate the corrective offset image data 401. In addition, it is assumed that in all the offset data, the random noise is equal to σ random, and the line noise is equal to σ Line. At that time, the line noise of the corrective offset image data is (σ Line/$\sqrt{N}$), and the ratio of the line noise to the random noise of the corrective offset image data is $(1/\sqrt{N}) \times (\sigma$ Line/σ random).

Further, it is assumed that the values of the random noise and line noise of the image data are the same as those of the offset image data. In this case, according to the second exemplary embodiment, in the corrected image data after an offset correction, the line noise is $(\sqrt{((N+1)/N)})\sigma$ Line, and the ratio of the line noise to the random noise is $(\sqrt{(N+1)/N)}) \times (\sigma$ Line/σ random). Therefore, by increasing the number of offset data used for a correction, the time and memory capacity needed for acquisition of the offset image data are increased, but the line noise and the ratio of the line noise to the random noise after an offset correction can be reduced and an excellent image can be acquired.

Note that by not storing in the offset memory the offset data that is not used for the generation of the corrective offset image data among the acquired offset image data, corrective offset image data can be generated as long as there is the same amount of memory as the corrective offset image data. In this case, only time needed for acquisition of the offset image data is increased, and the line noise and the ratio of the line noise to the random noise in the image after the offset correction can be reduced.

Figure 10:
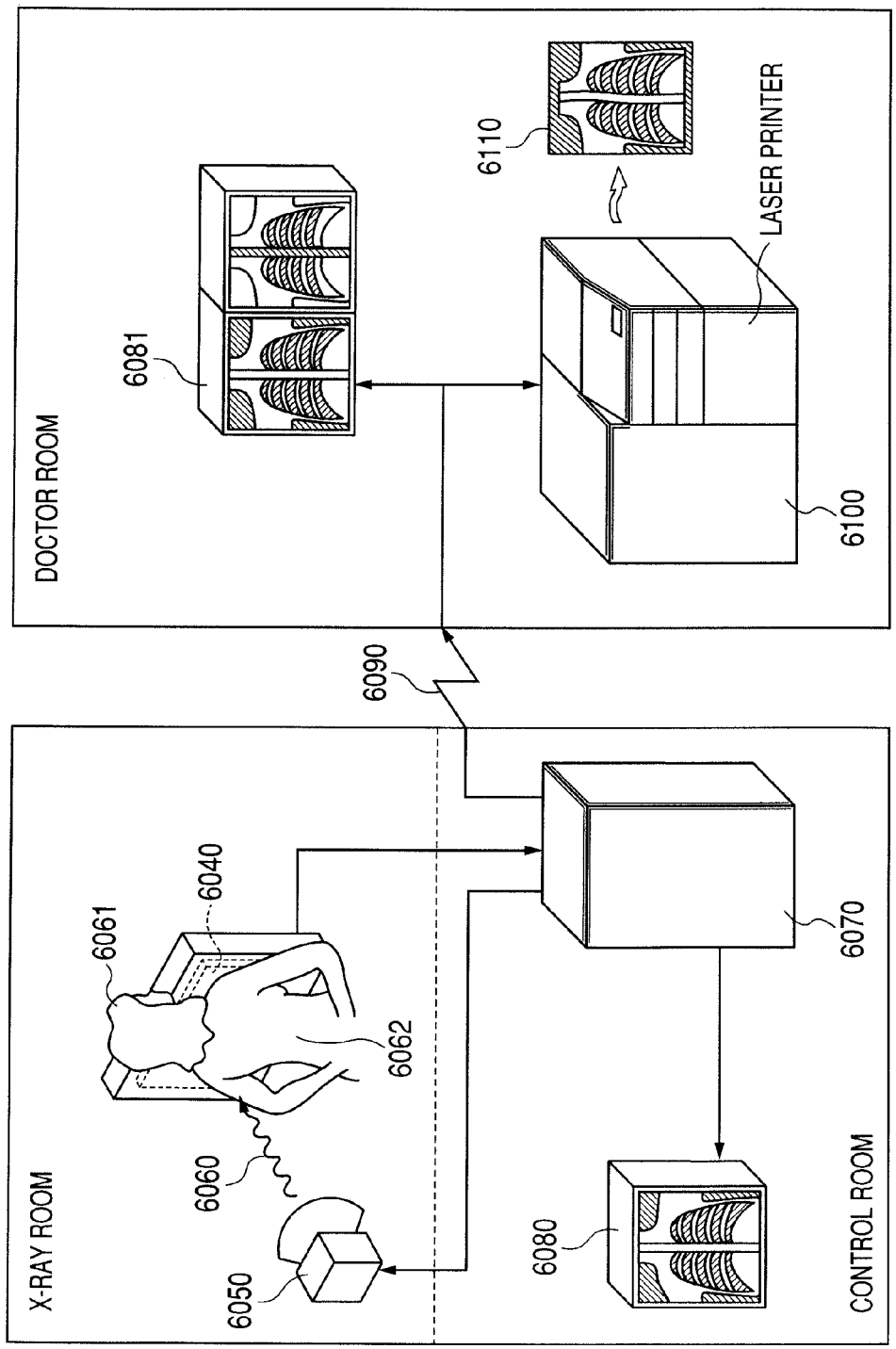
FIG. 10 is a diagram illustrating an example of a structure of an imaging system where the imaging apparatus according to the exemplary embodiment of the present invention is applied.

Next, an imaging system to which the imaging apparatus according to each exemplary embodiment described above is applied will be described. FIG. 10 is a diagram illustrating an example of a structure of an imaging system.

In FIG. 10, an X-ray 6060 generated in an X-ray tube 6050 passes through the chest 6062 of a patient or subject 6061, and enters an image sensor 6040 having an imaging apparatus according to the exemplary embodiments of the present invention. The image sensor 6040 includes the conversion circuit 101, the drive circuit 102, the read out circuit 105 and the signal processing circuit 106 according to the exemplary embodiments described above. The incident X-ray includes the information on the inner body of the patient 6061. A scintillator (phosphor) emits light in response to the incident of the X-ray, and the photoelectric conversion element Sm-n of the conversion circuit 101 photoelectrically converts the X-ray in order to acquire electric information.

The image sensor 6040 outputs the information to the image processor 6070 as an electric signal (digital signal). The image processor 6070 applies image processing to the received signal, which is in turn output to a display 6080 in a control room. The user observes an image displayed on the display 6080 to acquire information on the inner body of the patient 6061. Note that the image processor 6070 also has various control functions, and can switch movie/still picture shooting modes, and control the X-ray tube (radiation generator) 6050.

The image processor 6070 can transfer the electric signals output from the image sensor 6040 to a remote location through a transmission processing unit such as a phone line 6090, and show them on the display 6081 located in another place such as a doctor room. The electric signals output from the image sensor 6040 may be saved in a storage unit such as an optical disk so that a doctor in a remote place can use the storage unit to make a diagnosis. The electric signals may be recorded also in a film 6110 by a film processor 6100.

Note that in each exemplary embodiment described above, the structure of a photoelectric conversion element is not particularly limited. For example, a photoelectric conversion element may be used, the main material of which is amorphous silicon over an insulating substrate, having a wavelength converter for converting a radiation into a light in a wavelength band that the photoelectric conversion element can detect, and a photoelectric converter for receiving a light and converting the light into an electric charge. As such an element, for example, a PIN-type photoelectric conversion element including a P layer in which accepter impurities are doped, an I layer which is an intrinsic semiconductor layer, and an N layer in which donor impurities are doped, can be cited. Moreover, there can be cited an MIS-type photoelectric conversion element including a metal thin film layer formed on a substrate, an insulating layer, which is made of amorphous silicon nitride preventing the passage of electrons and holes, a semiconductor layer, which is made of hydrogenated amorphous silicon, an N type impurity semiconductor layer, which prevents the injection of holes, and a conductive layer.

In the MIS-type photoelectric conversion element, the conductive layer may be a transparent conductive layer, and the conductive layer may be formed in a part of the injection preventing layer. When these photoelectric conversion elements are used as a conversion element, and a wavelength converter is needed, as a wavelength converter, a phosphor made of $Gd_2O_2S$, $Gd_2O_3$ or CsI as the main components can be used. Furthermore, an element which includes amorphous selenium, gallium arsenide, lead iodide or mercury iodide as the material of a semiconductor layer, and absorbs an irradiated radiation to convert the absorbed radiation into an electric signal directly without using any wavelength converters may be used as a conversion element.

Moreover, the structure of the read out circuit 105 is not particularly limited either. For example, the read out circuit 105, which includes an amplifying unit for amplifying signals read out from the conversion circuit 101, an accumulation unit for accumulating the signal amplified by the amplified unit, and a serial conversion unit for performing the serial conversion of the signal accumulated by the accumulated unit, can be applied.

Other Exemplary Embodiments of the Present Invention

So as to operate the various devices in order to realize the functions of the exemplary embodiments, a software program of realizing the functions of the exemplary embodiments is provided to a computer (CPU or MPU) within an apparatus or a system connected to various devices. In addition, those carried out by operating the various devices according to the program stored in the computer in the system or apparatus are also included in the present invention.

In this case, since the program itself of the software realizes the functions of the exemplary embodiments, the program itself constitutes the present invention. A unit for supplying the program to the computer, for example, a storage medium for storing such a program constitutes the present invention. As a storage medium for storing such a program, a flexible disk, a hard disk, an optical disk, a magnet-optical disk, a CD-ROM, a magnetic tape, a non-volatile memory card, and a ROM may be used.

It goes without saying that when the functions of the exemplary embodiments are realized by a supplied program in cooperation with the operating system or another application software running on the computer, such program is also included in the exemplary embodiments of the present invention.

In addition, after the supplied program has been stored in a memory provided on a function expansion board or a function expansion unit related to a computer, a CPU provided on the function expansion board performs the entirety or a portion of the actual processing based on the instruction of the program. It goes without saying that when the functions of the exemplary embodiments are realized by this processing, the embodiment is also included in the present invention.

For example, the functions of the control circuit 108 and the signal processing circuit 106 are realized by a computer function having CPU, ROM, and RAM. The present invention also includes cases where the processing program for performing such processing operations as described above is stored in a ROM, and the CPU reads out from the ROM and executes the processing program to carry out the controls to realize the processing operation.

Note that since the exemplary embodiments illustrate only few examples of implementations for carrying out the present invention, the technical scope of the present invention is not limited thereby. That is to say, the present invention can be carried out in various forms, without departing from the spirit and scope of the invention.

INDUSTRIAL APPLICABILITY

An imaging apparatus according to each exemplary embodiment of the present invention is suitable for a radiation imaging apparatus for photographing a radiation image, and a radiation imaging apparatus used for medical diagnosis and industrial nondestructive inspection.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2008-014194, filed Jan. 24, 2008, which is hereby incorporated by reference herein in its entirety.

The invention claimed is:

1. An imaging apparatus comprising:
a conversion unit having a plurality of pixels arranged in a matrix, each pixel including a conversion element converting radiation or light into an electric charge;
a read-out unit for reading out an electric signal group according to the plurality of conversion elements based on the electric charge of conversion elements;
a control unit for conducting selectively a first read-out operation and a second read-out operation, wherein the first read-out operation is an operation for reading out a first electrical signal group from the conversion unit irradiated with the radiation or light by the read-out unit, the second read-out operation is an operation for reading out a second electrical signal group from the conversion unit without the conversion unit being irradiated with the radiation or light by the read-out unit, and the control unit conducts a control to repeat at a plurality of times the second read-out operation; and
a signal processing unit for processing the electric signal group outputted from the read-out unit,
wherein the signal processing unit generates a third electric signal group by deriving, from the plurality of the second electric signal groups, electric signals, each one corresponding to each one of the pixels, such that not all electric signals of the pixels in a row of the matrix are derived from one of the plurality of second electric signal groups, and the signal processing unit subtracts the third electric signal group from the first electric signal group.

2. The imaging apparatus according to claim 1, wherein the signal processing unit subjects the second electric signal group to a correction processing, and generates the third electric signal group based on the second signal group subjected to the correction processing.

3. The imaging apparatus according to claim 1, wherein the signal processing unit generates the third electric signal group by deriving the electric signals, such that the electric signals derived from the one of the plurality of second electric signal groups are not adjacent to each other in a row direction.

4. The imaging apparatus according to claim 1, wherein the signal processing unit generates the third electric signal group by deriving the electric signals, such that the electric signals derived from two of the plurality of second electric signal groups are alternatingly arranged in a row direction and a column direction.

5. The imaging apparatus according to claim 1, wherein the signal processing unit generates the third electric signal group by deriving the electric signals, at random from the plurality of second electric signal groups.

6. The imaging apparatus according to claim 1, wherein the signal processing unit generates the third electric signal group by deriving, from each of the plurality of second electric signal groups, the same number of the electric signals as the number of the second electric signal groups.

7. The imaging apparatus according to claim 1, wherein the control unit conducts at least once a second read-out operation before and after the first read-out operation.

8. The imaging apparatus according to claim 1, wherein the conversion unit includes switch elements each included in each of the pixels, a driving unit for driving the conversion unit, a driving wiring connected commonly to the plurality of the switch elements in a row direction and a signal wiring connected between the read-out unit and the plurality of the switch elements in a column direction.

9. The imaging apparatus according to claim 1, wherein the conversion element includes a wavelength converter for wavelength converting the radiation incident thereon into the light and a photoelectric conversion element for converting the light into the electric charge.

10. The imaging apparatus according to claim 1, further comprising a driving unit for driving the conversion unit.

11. An imaging system comprising:
an imaging apparatus according to claim 1; and
a radiation generator for generating the radiation.

12. A signal processing method in driving an imaging apparatus comprising a conversion unit having a plurality of pixels arranged in a matrix, each pixel including a conversion element converting radiation or light into an electric charge, and a read-out unit for reading out an electric signal group according to the plurality of conversion elements based on the electric charge of conversion elements, wherein the method comprises:
a first read-out step of reading out, by the read-out unit, the electrical signal group from the conversion unit irradiated with the radiation or light, and outputting the electrical signal group as a first electrical signal group;
a second read-out step of reading out, by the read-out unit, the electrical signal group from the conversion unit without the conversion unit being irradiated with the radiation or light, and outputting the electrical signal group as a second electrical signal group; and
a signal processing step of repeating at a plurality of times the second read-out step, generating a third electric signal group by deriving, from the plurality of the second electric signal groups, electric signals, each one corresponding to a respective one of the pixels, such that not all electric signals of the pixels in a row of the matrix are derived from one of the plurality of second electric signal groups, and subtracting the third electric signal group from the first electric signal group.

13. A non-transitory computer-readable recording medium storing, in executable form, a program for causing a computer to execute a signal processing method in driving an imaging apparatus comprising conversion unit having a plurality of pixels arranged in a matrix, each pixel including a conversion element converting radiation or light into an electric charge, and a read-out unit for reading out an electric signal group according to the plurality of conversion elements based on the electric charge of conversion elements, wherein the program causes the computer to execute:
a first read-out step of reading out, by the read-out unit, the electrical signal group from the conversion unit irradiated with the radiation or light, and deriving the electrical signal group as a first electrical signal group;
a second read-out step of reading out, by the read-out unit, the electrical signal group from the conversion unit without the conversion unit being irradiated with the radiation or light, and deriving the electrical signal group as a second electrical signal group; and
a signal processing step of repeating at a plurality of times the second read-out step, generating a third electric signal group by deriving, from the plurality of the second electric signal groups, electric signals, each one corresponding to a respective one of the pixels, such that not all electric signals of the pixels in a row of the matrix are derived from one of the plurality of second electric signal groups, and subtracting the third electric signal group from the first electric signal group.

14. An imaging apparatus comprising:
a conversion unit having a plurality of pixels arranged in a matrix, each pixel converting radiation or light into an electric charge, wherein the conversion unit outputs electrical signals row-by-row from the matrix based on the electric charges of the pixels;
a control unit for conducting a read-out operation that outputs the electrical signals from the conversion unit together as an electric signal group, wherein the control unit conducts (1) a single first read-out operation that outputs, from the conversion unit irradiated with radiation or light, the electric signal group as a first electric signal group, and (2) a plurality of second read-out operations, each second read-out operation outputting the electric signal group as a second electric signal group and each second read-out operation being different from the first read-out operation; and
a signal processing unit for processing electic signal groups, wherein the signal processing unit generates a third electric signal group by deriving, from one of the plurality of the second electric signal groups, an electric signal corresponding to at least one of the pixels, and the signal processing unit conducts a subtraction with the third electric signal group and the first electric signal group.

15. The imaging apparatus according to claim 14, wherein the signal processing unit subjects the second electric signal group to a correction processing, and generates the third electric signal group based on the second electric signal group subjected to the correction processing.

16. The imaging apparatus according to claim 14, wherein the signal processing unit generates the third electric signal group by deriving the electric signals, such that the electric signals derived from the one of the plurality of second electric signal groups are not adjacent to each other in a row direction.

17. The imaging apparatus according to claim 14, wherein the signal processing unit generates the third electric signal group by deriving the electric signals, such that the electric signals derived from two of the plurality of second electric signal groups are alternatingly arranged in a row direction and a column direction.

18. The imaging apparatus according to claim 17, wherein the signal processing unit generates the third electric signal group by deriving, from each of the plurality of second electric signal groups, approximately a same number of the electric signals.

19. The imaging apparatus according to claim 14, wherein the signal processing unit generates the third electric signal group by deriving, from each of the plurality of second electric signal groups, the same number of the electric signals as the number of the second electric signal groups.

20. An imaging system comprising:
an imaging apparatus according to claim 14; and
a radiation generator for generating the radiation.

* * * * *